United States Patent
Takino (10) Patent No.: US 8,585,670 B2
(45) Date of Patent: Nov. 19, 2013

(54) DISPOSABLE PANTS-TYPE BODY FLUID ABSORBENT WEARING ARTICLE

(75) Inventor: Shunsuke Takino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 679 days.

(21) Appl. No.: 12/676,419

(22) PCT Filed: Jul. 11, 2008

(86) PCT No.: PCT/JP2008/062553

§ 371 (c)(1),
(2), (4) Date: Jun. 10, 2010

(87) PCT Pub. No.: WO2009/031360

PCT Pub. Date: Mar. 12, 2009

(65) Prior Publication Data

US 2010/0249743 A1   Sep. 30, 2010

(30) Foreign Application Priority Data

Sep. 5, 2007   (JP) .................. 2007-230710

(51) Int. Cl.
*A61F 13/15*   (2006.01)

(52) U.S. Cl.
USPC ............ 604/385.28; 604/385.04; 604/385.24; 604/385.27; 604/385.29

(58) Field of Classification Search
USPC ............. 604/385.04, 385.24, 385.27, 385.28, 604/385.29
See application file for complete search history.

(56) References Cited

U.S. PATENT DOCUMENTS 5,085,654 A  *  2/1992  Buell ........................ 604/370
7,060,058 B2     6/2006  Otsubo et al.

FOREIGN PATENT DOCUMENTS

| JP | 2002-306534 A | 10/2002 |
| JP | 2003-265511 A | 9/2003 |
| JP | 2004-329238 A | 11/2004 |

OTHER PUBLICATIONS

PCT/JP2008/062553 International Search Report, mailed Oct. 7, 2008.

* cited by examiner

*Primary Examiner* — Jacqueline F. Stephens
(74) *Attorney, Agent, or Firm* — Lowe Hauptman & Ham, LLP (57) ABSTRACT

In a disposable pants-type wearing article, a body fluid absorbent panel provided in a crotch region extends in a longitudinal direction A and is fixed to a sheet member defining inner surfaces of front and rear waist regions. The body fluid absorbent panel is formed along its opposite side edges with flaps and free edges of the respective flaps are provided with crotch region elastic members attached under tension thereto. The front and rear waist regions are provided along peripheral edges of leg-openings with lower elastic members attached under tension thereto. Regions of the side flaps in which the free edges of the flaps developed in a transverse direction overlap the associated lower elastic members are affixed to respective inner surfaces of the front and rear waist regions.

10 Claims, 7 Drawing Sheets

(Prior Art)

FIG.7

(Prior Art)

DISPOSABLE PANTS-TYPE BODY FLUID ABSORBENT WEARING ARTICLE

RELATED APPLICATIONS

The present application is based on International Application PCT/JP2008/062553, filed Jul. 11, 2008 and claims priority from Japanese Application Number 2007-230710, filed Sep. 5, 2007, the disclosures of which are hereby incorporated by reference herein in their entirety.

TECHNICAL FIELD

The present invention relates generally to a disposable pants-type body fluid absorbent wearing article suitable to be used as a disposable diaper, disposable pants for incontinent patient or the like.

RELATED ART

Pants-type diapers as the typical embodiment of the disposable pants-type body fluid absorbent wearing articles are well known. The diaper of such type is exemplarily disclosed in Japanese Unexamined Patent Application Publication No. 2003-265511 (PATENT DOCUMENT 1).

Figure 6:
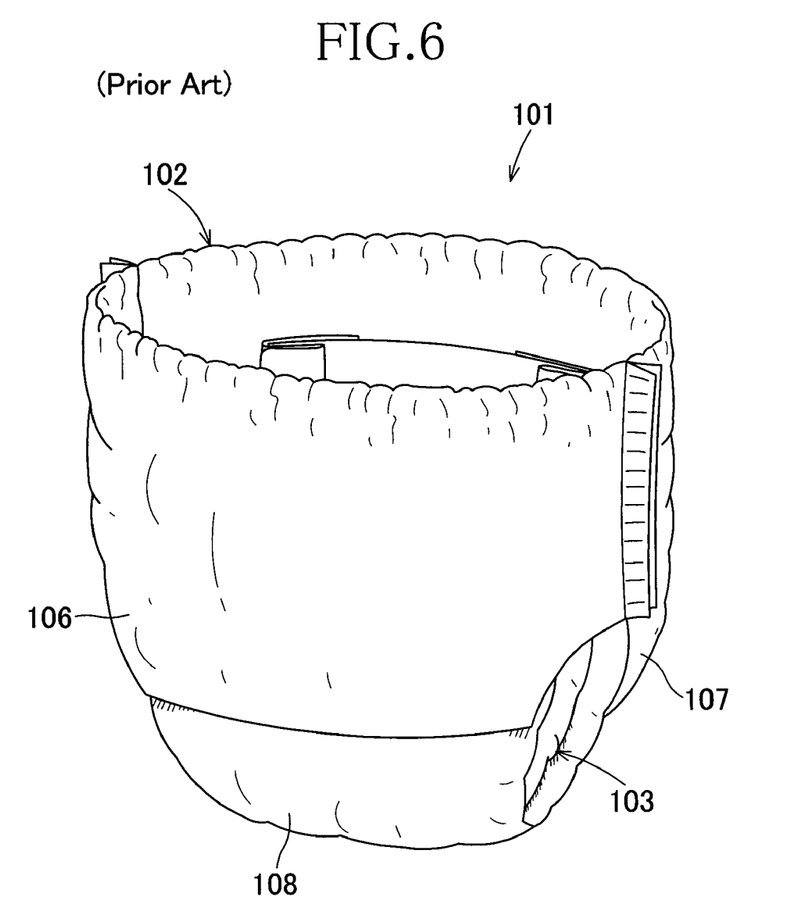
FIG. 6 is a partially cutaway perspective view of a pants-type diaper of prior art.
Figure 7:
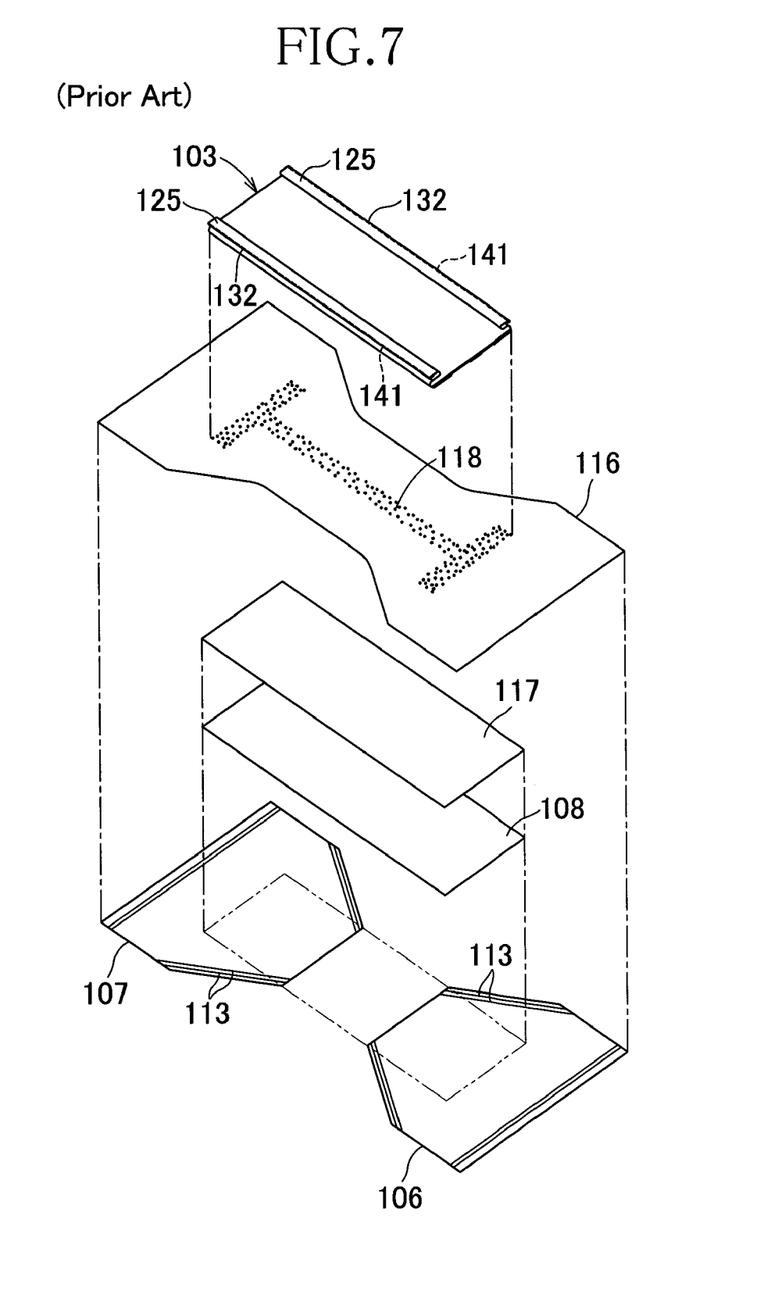
FIG. 7 is an exploded perspective view of the diaper illustrated by FIG. 6.

FIGS. 6 and 7 of the accompanying drawings are perspective and exploded views, respectively, illustrating a pants-type diaper 101 disclosed in the above-identified Publication. The diaper 101 comprises a covering chassis 102 adapted to cover the wearer's body and a body fluid absorbent panel 103. The covering chassis 102 comprises, in turn, a hexagonal front sheet 106 defining a front waist covering region and a part of a crotch covering region, a hexagonal rear sheet 107 defining a rear waist covering region and a part of the crotch covering region and a rectangular center sheet 108 defining the remaining part of the crotch covering region. The front and rear sheets 106, 107 are respectively provided with leg elastic members 113 attached under tension thereto. The center sheet 108 has its opposite end portions bonded to the inner surfaces of the front and rear sheets 106, 107. A rectangular water-barrier film 117 and an hourglass-shaped sheet 116 are placed upon the inner surface of the center sheet 108. The rectangular body fluid absorbent panel 103 is bonded to the inner surface of the hourglass-shaped sheet 116 by hot melt adhesive 118. The body fluid absorbent panel 103 is formed along its opposite side edges with flaps 125. These flaps 125 are provided along side edges 132 thereof with elastic members 141 attached under tension thereto. In the state of the diaper 101 illustrated in FIG. 6, the body fluid absorbent panel 103 bows substantially in a U-shape and the flaps 125 and the flaps 125 rise up on the inner surface of the body fluid absorbent panel 103 as the elastic members 141 contract from the stretched state as shown in FIG. 7. In this way, the flaps 125 form leak-barriers against sideway leakage of body fluids. In such diaper 101, the elastic members 141 associated with the respective flaps 125 also describe a U-shape. In the diaper 101 put on the wearer's body, the elastic members 141 extend upward so as to go halves around the respective legs in groins of the wearer. Portions of the elastic members 141 extending upward overlap the leg elastic members 113 provided on the front and rear sheets 106, 107 by the intermediary of various sheets such as the center sheet 108 and thereby ensure that the diaper 101 comes in close contact with the wearer's legs over entire circumferences thereof.

PATENT DOCUMENT 1: Japanese Unexamined Patent Application Publication No. 2003-265511

DISCLOSURE OF THE INVENTION

Problem to be Solved by the Invention

In the pants-type diaper of prior art illustrated in FIGS. 6 and 7, the leg elastic members are divided into three groups consisting of those attached to the front sheet, those attached to the rear sheet and those attached to the center sheet wherein the respective groups extend rectilinearly. The diaper having the leg elastic members in such arrangement facilitates continuous production of the diaper at a high-speed. In this diaper put on the wearer's body, under the effect of the elastic members attached to the flaps of the body fluid absorbent panel, the free edges of the flaps are held upward in close contact with the wearer's groins so that leakage of body fluids from the groins can be prevented. However, if the diaper more or less slips down after the diaper has been put on the wearer's body, the free edges of the flaps also may slip down so as to be spaced from the groins, resulting in leakage of body fluids beyond the leg-openings.

In view of the problem as has been described above, it is an object of the present invention to improve the known wearing article as has been exemplarily described above so that leakage of body fluids otherwise occurring beyond the leg-openings can be reliably prevented even if the waist region of the wearing article slip down after the diaper has been put on the wearer's body.

Measure to Solve the Problem

The object set forth above is achieved according to the present invention by improvement in the disposable pants-type body fluid absorbent wearing article having a longitudinal direction, a transverse direction and a vertical direction being orthogonal one to another, comprising front and rear waist regions and a crotch region combined to define a pants-like shape having a waist-opening and a pair of leg-openings, wherein a body fluid absorbent panel provided in the front waist region extends in the longitudinal direction and is affixed to sheet members defining respective inner surfaces of the front and rear waist regions and wherein the front and rear waist regions are elasticized along a peripheral edge of the waist-opening and respective peripheral edges of the leg-openings.

The improvement according to the present invention is characterized in aspects as will be described below: the body fluid absorbent panel comprises a body fluid absorbent core, a liquid-pervious sheet used to wrap the core, a body fluid absorbent pad extending in the longitudinal direction and bonded to respective the inner surfaces of the front and rear waist regions and flaps formed along side edges of the body fluid absorbent pad opposed in the transverse direction, the flaps respectively comprising proximal edges being contiguous to the side edges of the body fluid absorbent pad and extending in the longitudinal direction and free edges, each at a distance from the body fluid absorbent pad in the transverse direction, extending in parallel to the proximal edges; the free edges are provided with first elastic members attached under tension thereto; and the front and rear waist regions are provided along the peripheral edges of the leg-openings with second elastic members attached under tension thereto so as to intersect the side edges of the body fluid absorbent pad and regions of the flaps in which the free edges of the flaps developed outward in the transverse direction overlap the second elastic members are affixed to the inner surfaces of the front and rear waist regions.

According to one preferred embodiment of the present invention, the front and rear waist regions as well as the body fluid absorbent panel are shaped in rectangles.

According to another preferred embodiment of the present invention, a dimension between the proximal edge and the free edge of the flap as measured in the transverse direction is in a range of 15 to 50 mm.

Effect of the Invention

The disposable pants-type body fluid absorbent wearing article is characterized in that the flaps formed along the opposite side edges of the body fluid absorbent pad in the body fluid absorbent panel are provided along the free edges thereof with the first elastic members attached under tension thereto and these free edges and the regions of the flaps in which the free edges of the flaps developed outward in the transverse direction overlap the second elastic members are affixed to the inner surfaces of the front and rear waist regions. With such unique arrangement, the free edges of the flaps also are pulled in the transverse direction as this wearing article is put on the wearer's body and thereupon the front and rear waist regions are pulled in the transverse direction, ensuring that the free edges lying in the crotch region sideways come in close contact with the wearer's groins. Provided with these flaps of which the free edges behave in the manner as has been described above, even when the pants-type body fluid absorbent wearing article of the invention more or less slips down after it has been put on the wearer's body, the free edges of the flaps hardly slip down and there is no anxiety that leak of body fluids might occur beyond these free edges. Even if the free edges of the flaps slip down, the free edges maintain in close contact with the wearer's legs and leak of body fluids beyond the leg-openings can be reliably prevented.

The other advantageous effects provided by the present invention will be understood from the description made hereunder.

IDENTIFICATION OF REFERENCE NUMERALS USED IN THE DRAWINGS 1 pants-type diaper
2 waist region (covering member)
3 body fluid absorbent panel (panel member)
11 sheet member (inner sheet)
15b second elastic members (lower elastic members)
23 intermediate region
24 side flaps
27 waist-opening
28 leg-openings
31 liquid-pervious sheet (inner cover sheet)
33 core
33a side edges
40a proximal edge
40b free edge
43 first elastic members (crotch region elastic members)
A longitudinal direction
B transverse direction
C vertical direction

DESCRIPTION OF THE BEST MODE FOR WORKING OF THE INVENTION

Details of a disposable pants-type body fluid absorbent wearing article according to the invention will be more fully understood from the description of a pants-type diaper given hereunder as an embodiment of such wearing article with reference to the accompanying drawings.

Figure 1:
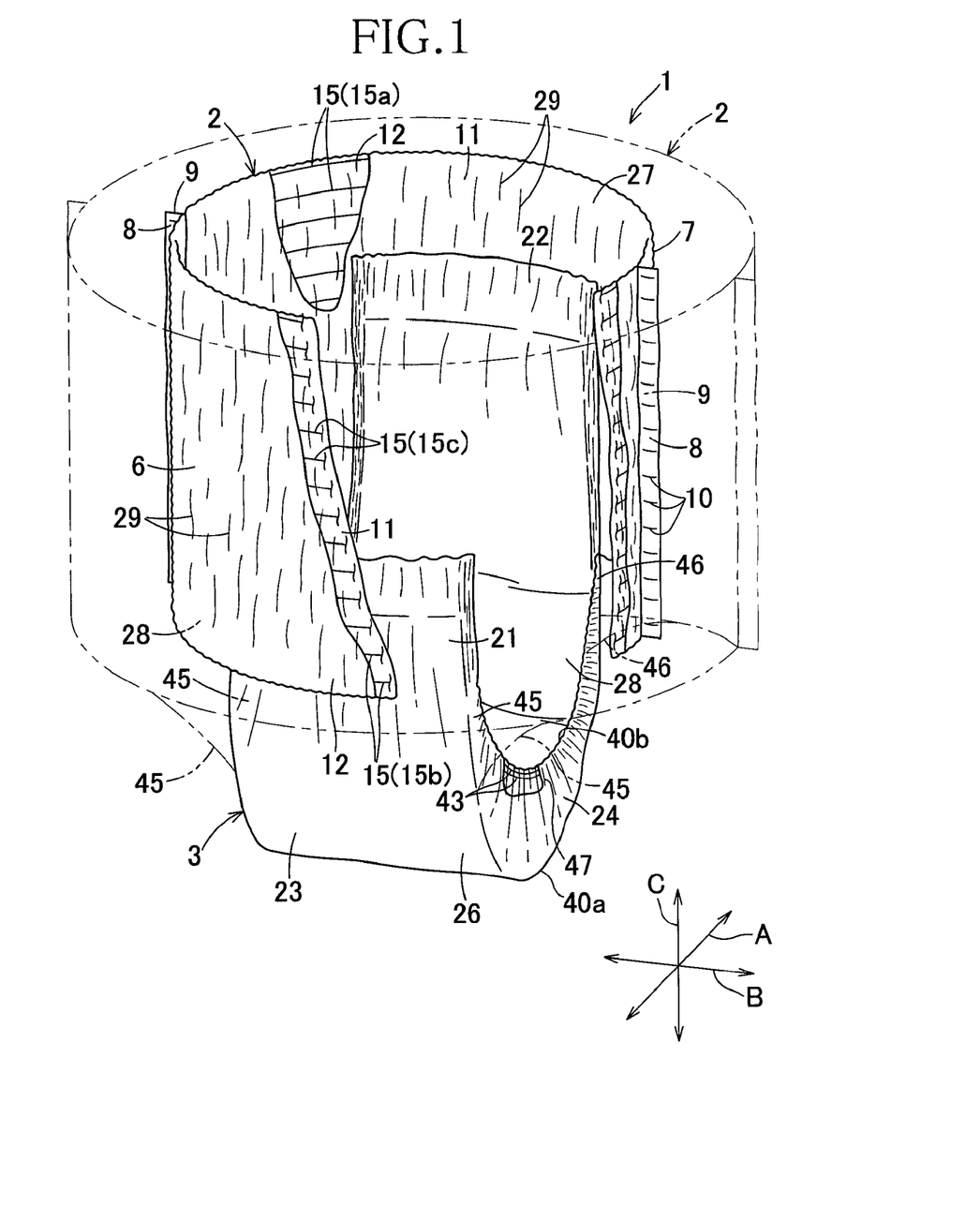
FIG. 1 is a partially cutaway perspective view of a pants-type diaper.

FIG. 1 is a partially cutaway perspective view of pants-type diaper 1. The pants-type diaper 1 comprises a waist region covering member 2 and a body fluid absorbent panel member 3. In FIG. 1, double-headed arrows A, B and C being orthogonal one to another respectively indicate longitudinal, transverse and vertical directions of the pants-type diaper 1. The waist region covering member 2 includes a front member 6 defining a front waist region and a rear member 7 defining a rear waist region. These members 6, 7 respectively have transversely opposite side edges 8, 8 and 9, 9 put flat and welded together along joints 10 lined up intermittently in the vertical direction C so as to form an annular structure. Each of the front member 6 and the rear member 7 comprises an inner sheet 11 and an outer sheet 12 bonded together and these inner and outer sheets 11, 12 sandwich therebetween a plurality of waist elastic members 15 extending under tension along a waist-surrounding direction. These elastic members 15 are attached at least to the inner sheet 11 by means of hot melt adhesive (not shown). The panel member 3 has a front end region 21 bonded to the inner sheet 11 of the front member 6 by means of hot melt adhesive 16 (See FIG. 3), a rear end region 22 bonded to the inner sheet 11 of the rear member 7 by means of hot melt adhesive 16 and an intermediate region 23 extending between these ends 21, 22 so as to define a crotch region. The panel member 3 is formed along both sides thereof in the transverse direction B with side flaps 24 between which a body fluid absorbent pad 26 extends. The side flaps 24 form leakage-barriers 24 adapted to prevent body fluids from flowing on the inner surface of the body fluid absorbent pad 26 in the transverse direction B and, in consequence, leaking sideways.

In the pants-type diaper 1 comprising the front member 6, the rear member 7 and the panel member 3 in the manner as has been described above, the front member 6 and the rear member 7 cooperate with each other to form a waist-opening 27 while the front member 6, the rear member 7 and the panel member 3 cooperated together to form a pair of leg-openings 28. The waist region covering member 2 is formed with a plurality of gathers 29 as the elastic members 15 contract. Imaginary lines indicate the waist region covering member 2 with its diameter enlarged as the diaper 1 is put on the wearer's body.

Figure 2:
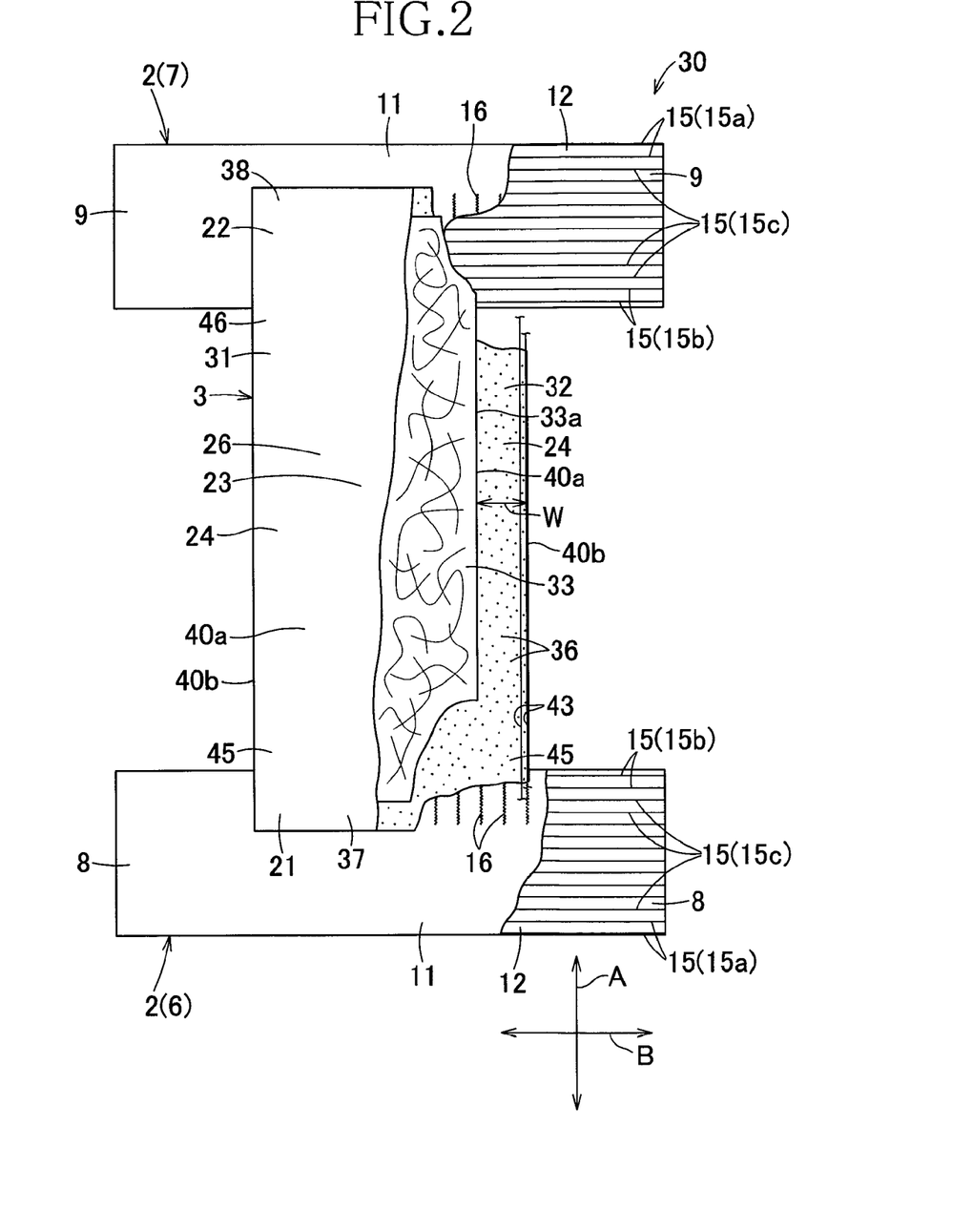
FIG. 2 is a partially cutaway plan view of the diaper developed and flattened.

FIG. 2 is a partially cutaway plan view of the diaper 30 corresponding to the diaper 1 of FIG. 1 with the front member 6 and the rear member 7 disjoined from each other along the joints and flatly developed together with the panel member 3 in the longitudinal direction A as well as in the transverse direction B. The front member 6 and the rear member 7 are of the same rectangular shape and of the same size. The elastic members allocated to the respective members 6, 7 comprise upper elastic members 15a extending along the peripheral edge of the waist-opening 27 across the member 6 or 7, lower elastic members 15b extending along the peripheral edges of the leg-openings 28 across the member 6 or 7 so as to intersect with side edges 33a of a core 33 defining respective side edges of the body fluid absorbent pad 26, and intermediate elastic members 15c circumferentially extending in the waist-surrounding direction between the upper and lower elastic members 15a, 15b. As will be seen in FIG. 2, some of the intermediate elastic members 15c intersect with the side edges 33a of the core 33 and the other thereof do not intersect with the side edge 33a of the core 33. The number as well as the extensibility of the elastic members respectively constituting the upper, lower and intermediate elastic members 15a, 15b, 15c may be selected so that a desired fit of the waist region covering member 2 to the wearer's body can be obtained. The inner sheet 11 and the outer sheet 12 in the front member 6 and the rear member 7 are formed by a sheet material such as a nonwoven fabric, a woven fabric or a plastic film, preferably by an appropriate air-permeable sheet material. The sheet material is preferably made of thermoplastic synthetic resin allowing the sheet materials to be welded to each other.

The panel member 3 also is of a rectangular shape and comprises a liquid-pervious inner cover sheet 31, a liquid-impervious outer cover sheet 32 and the liquid-absorbent core 33 sandwiched between these cover sheets 31, 32. The inner cover sheet 31 and the outer cover sheet 32 extend outward beyond a peripheral edge of the substantially rectangular core 33, then put flat together outside the peripheral edge of the core 33, and bonded together by means of hot melt adhesive 36 to form a pair of the side flaps 24, a front end flap 37 and a rear end flap 38. Each of these side flaps 24 extends outward in the transverse direction B from the associated side edge 33a of the core 33 and has a proximal edge 40a defined adjacent the associated side edge 33a of the core 33 and free edge 40b extending in the longitudinal direction A in parallel to the proximal edge 40a. Along the free edge 40b, at least one crotch region elastic member 43 is sandwiched between the inner cover sheet 31 and the outer cover sheet 32 so as to extend in the longitudinal direction A. This crotch region elastic member 43 is attached under tension to at least one of these cover sheets 31, 32 by means of hot melt adhesive (not shown). A dimension W from the proximal edge 40a to the free edge 40b of the side flap 24 is substantially in a range of 15 to 50 mm depending on the diaper made for baby or for adult.

Of the panel member 3, the front end region 21 overlaps the front member 6 and is bonded to the latter wherein the outer cover sheet 32 in the front end region 21 is bonded to the inner sheet 11 of the front member 6 by means of hot melt adhesive 16 applied on the inner sheet 11 in a region of the front member 6 overlapped by the front end region 21 to form a belt-shaped adhesive zone. In a similar fashion, the rear end region 22 overlaps the rear member 7 and is bonded to the latter wherein the outer cover sheet 32 in the rear end region 22 is bonded to the inner sheet 11 of the rear member 7 by means of hot melt adhesive 16 applied on the inner sheet 11 in a region of the rear member 7 overlapped by the rear end region 22. The front end region 21 comprises parts of the respective side flaps 24, the front end flap 37 and a part of the core 33 wherein the side flaps 24 extend in the transverse direction B and overlap in this state the lower elastic members 15b by the intermediary of the inner sheet 11. The side flaps 24 contract from this state toward the side edges 33a of the core 33 to form gathers 41 (See FIG. 3) as the lower elastic members 15b of the front member 6 contract in the transverse direction B. The rear end region 22 comprises parts of the respective side flaps 24 of the panel member 3, the rear end flap 38 and a part of the core 33 wherein the side flaps 24 extend in the transverse direction B and overlap in this state the lower elastic members 15b by the intermediary of the inner sheet 11. The side flaps 24 in the rear end region 22 contract from this state toward the side edges 33a of the core 33 to form gathers 42 (See FIG. 3) as the lower elastic members 15b of the rear member 7 contract.

Figure 3:
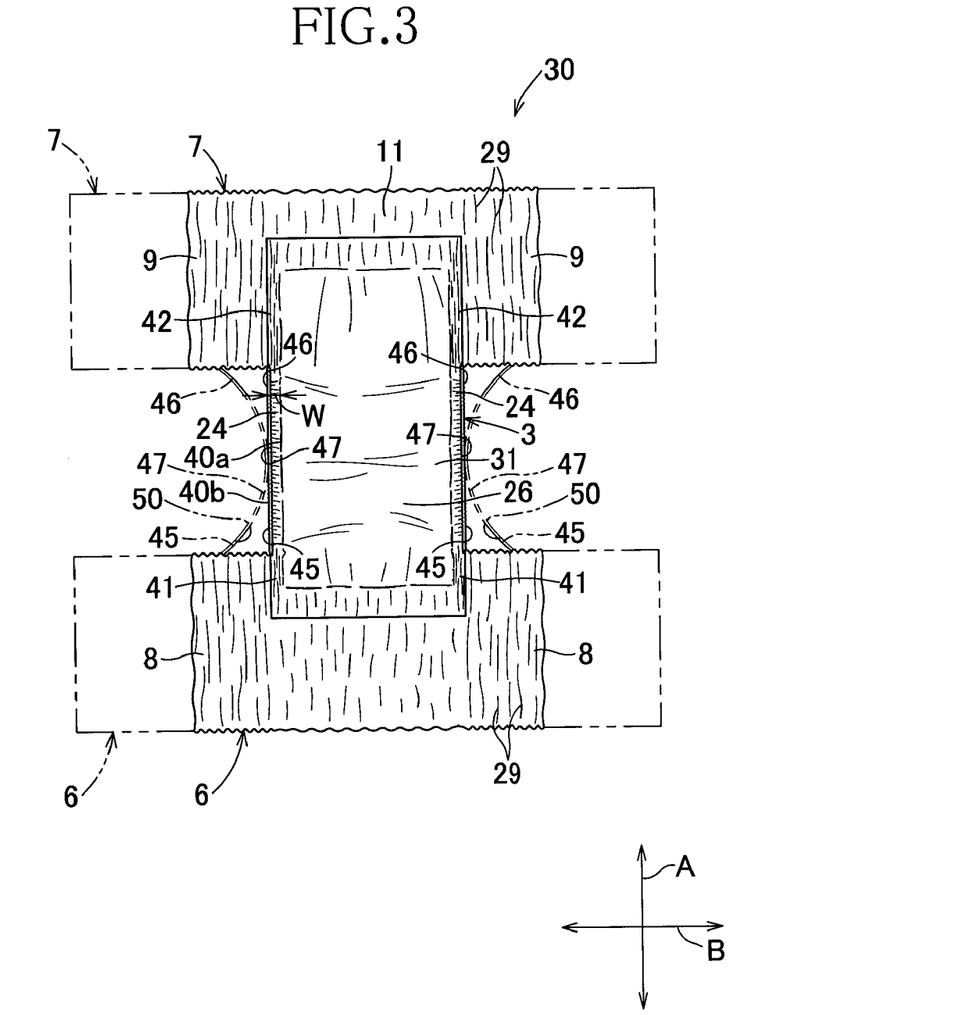
FIG. 3 is a plan view of the diaper developed but left elastically contract.

FIG. 3 is a plan view of the diaper 30 flatly developed as shown in FIG. 2 with the elastic members 15 and the crotch region elastic members left elastically contracted. From the diaper 30 flatly developed in this manner, the side edges 8 of the front member 6 may be joined with the side edges 9 of the rear member 6 to obtain the diaper 1 of FIG. 1. Referring to FIG. 3, contraction of the elastic members 15 causes the front member 6 and the rear member 7 to be formed with the gathers 29 as shown in FIG. 1 and, in consequence, apparent dimensions of these members 6, 7 in the transverse direction B are reduced with respect to actual dimensions thereof. Specifically, contraction of the crotch region elastic members 43 causes the panel member 3 to be bowed substantially in a U-shape with the outer cover sheet 32 outside, i.e., with the inner cover sheet 11 inside as seen in FIG. 1 and, in consequence, an apparent dimension of the panel member 3 in the longitudinal direction A is reduced with respect to an actual dimension thereof in FIG. 2. In the region of the panel member 3 overlapping the front member 6, the side flaps 24 comprising the inner cover sheet 31 and the outer cover sheet 32 both of which are easily deformable, shrink in the transverse direction B with formation of the gathers 41 as the lower elastic members 15b contract. Consequentially, the dimension W (See FIG. 2) measured between the proximal edge 40a and the free edge 40b is apparently reduced. Also in the region of the panel member 3 overlapping the rear member 7, the side flaps 24 shrink in the transverse direction B with formation of the gathers 42 and, in consequence, the dimension W is apparently reduced. The body fluid absorbent pad 26 in the panel member 3 is not so deformable as the side flaps 24 and serves to restrain contraction of the lower elastic members 15b and the intermediate elastic members 15c since this pad 26 extending between the side flaps 24, 24 contains the core 33 therein. Therefore, regions of the body fluid absorbent pad 26 respectively overlapping the front member 6 and the rear member 7 shrink in the transverse direction B at a factor substantially lower than that of the side flaps 24, 24. In consequence, none of gathers appears in these regions or, if appears, the number of gathers will be just a few. Referring to FIG. 3, the front member 6 and the rear member 7 both stretched in the transverse direction B and parts of the wearer's legs 50 are indicated by imaginary lines wherein these two members 6, 7 are stretched to the dimensions thereof as shown in FIG. 2. The wearer's legs 50 indicated by the imaginary lines suggest that the wearer's legs have been inserted into the respective leg-openings 28 (See FIG. 1) when the pants-type diaper 1 has been put on the wearer's body.

In the course of wearing the diaper 1 of FIG. 1 comprising the waist region covering member 2 and the panel member 3 constructed as has been described above, the waist region covering member 2 is deformed under stretching of the elastic members 15 to form a large annulus as indicated by imaginary lines in FIG. 1. The panel member 3 is introduced into the wearer's crotch region so that the side flaps 24 in the intermediate region 23 may be guided toward the wearer's groins (not shown) until the side flaps 24 come in contact with the wearer's groins. On the other hand, the side flaps 24 in the front end region 21 and the rear end region 22 are stretched in the transverse direction B so as to dissipate the gathers 41, 42 as seen in FIG. 3 under stretching of the lower elastic members 15b in the transverse direction B as viewed in FIG. 1 since the side flaps 24 in the front and rear end regions 21, 22 are integrated with the lower elastic members 15b by the intermediary of the inner sheet 11. In response to stretching of the side flaps 24 in the front and rear regions 21, 22, a portions 45 of the respective free edges 40b of the side flaps 24 in the intermediate region 23 lying in the vicinity of the lower elastic members 15b in the front member 6 and portions 46 thereof lying in the vicinity of the lower elastic members 15b in the rear member 7 (See FIGS. 1 and 2) are moved in the transverse direction B to the positions indicated by the imaginary lines in FIGS. 1 and 3. In this state, portions 47 defined between the portions 45 and the portions 46 are positioned between the wearer's legs 50 and come in close contact with the inner sides of the wearer's legs 50 in the vicinity of the respective groins. Specifically, in the case of the diaper 1 according to the invention, the elastically stretchable and contractible free edges 40b rather sideways come in close contact with the wearer's legs in the vicinity of the groins than coming in close contact from below with the wearer's legs. In this way, even when the diaper 1 more or less slips down after it has been put on the wearer's body, the free edges 40b of the side flaps 24 also would not be readily slipped down and body fluids would leak out through gaps which otherwise would be formed between the free edges 40b and the wearer's legs. Should the free edges 40b also slip down, such slippage will occur along the wearer's legs without being spaced from the wearer's legs. Therefore, in this case also, leakage of body fluids would not occur between the free edges 40b and the wearer's legs.

As will be understood from the foregoing description, the front and rear members 6, 7 as well as the panel member 3 in the diaper 1 of FIG. 1 are unexceptionally of simple rectangular structures allowing respective materials to be utilized substantially without incurring waste. In addition, the finished diaper 1 can prevent body fluids from leaking beyond the peripheries of the leg-openings.

Figure 4:
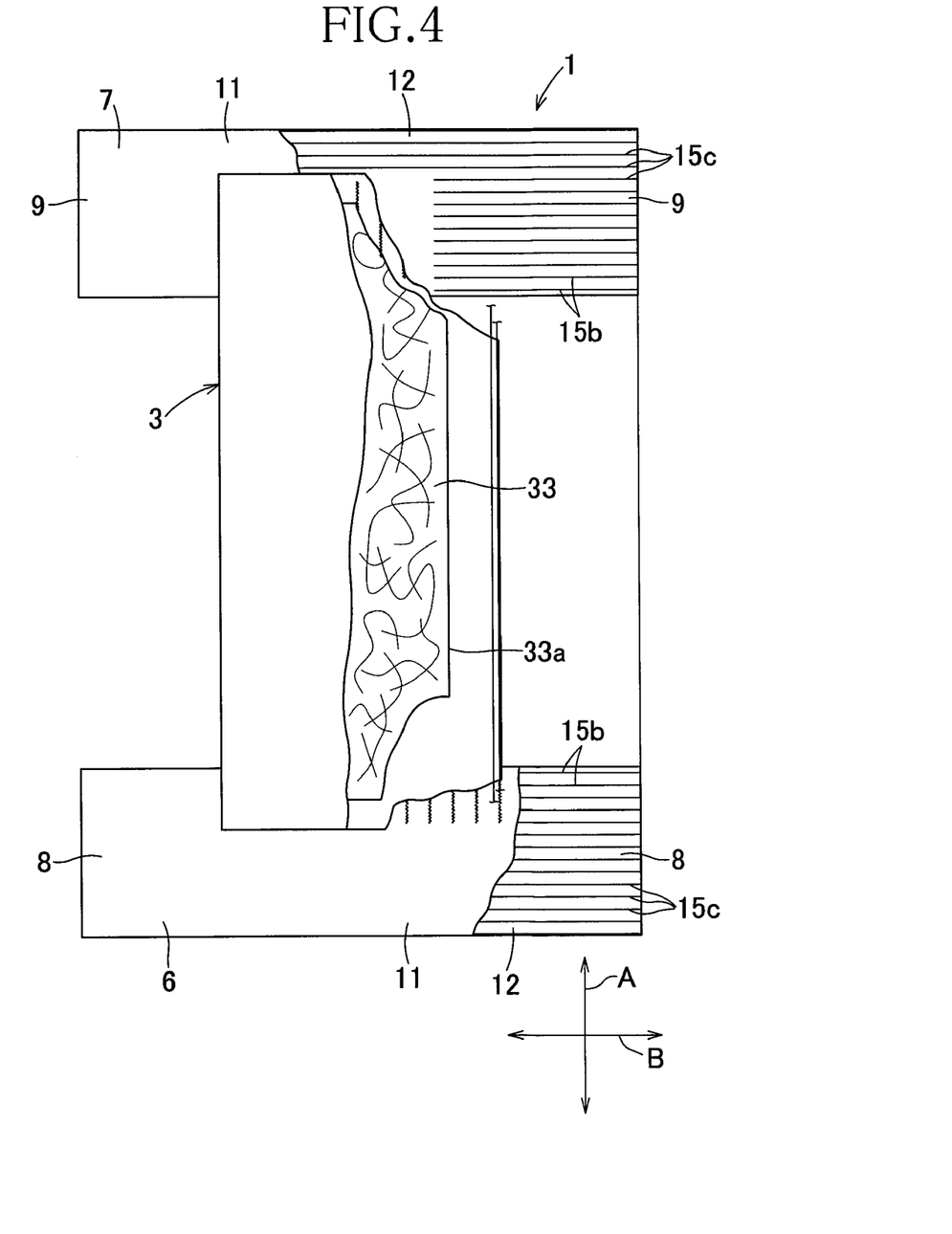
FIG. 4 is a view similar to FIG. 2, illustrating one preferred embodiment.

FIG. 4 is a view similar to FIG. 2, illustrating one preferred embodiment of the invention. In the pants-type diaper 1 of FIG. 4, the lower elastic members 15b and some of the intermediate elastic members 15c do not extend completely across the panel member 3 and rather extend from the side edges 8, 9 of the front and rear members 6, 7 to positions slightly beyond respective points of intersection with the side edges 33a of the core 33. The diaper 1 according to this embodiment is suitable to provide the outer surface of the outer sheet 12 with decorative picture or the like since the core 33 is hardly formed with gathers even when the lower elastic members 15b and the intermediate elastic members 15c have a relatively high contractile force.

Figure 5:
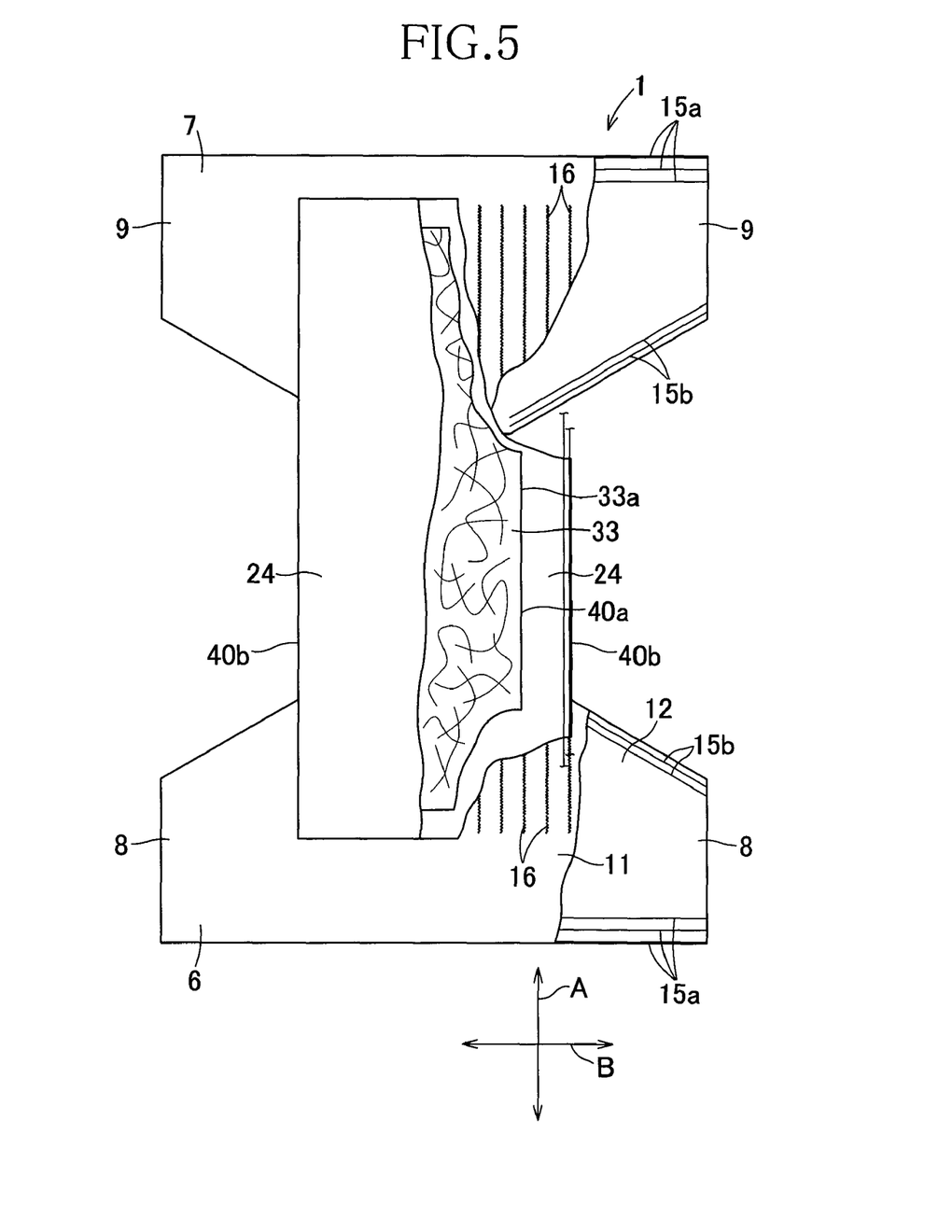
FIG. 5 is a view similar to FIG. 2, illustrating another preferred embodiment.

FIG. 5 also is a view similar to FIG. 2, illustrating another preferred embodiment of the invention. The front member 6 as well as the rear member 7 in the pants-type diaper 1 of FIG. 5 is shaped substantially in a hexagon. The lower elastic members 15b under tension obliquely extend from the side edges 8, 9 of the front and rear members 6, 7 to the side edges 33a of the core 33 contained in the panel member 3 and bonded to the inner sheet 11 and the outer sheet 12 by means of hot melt adhesive (not shown). The side flaps 24 are bonded to the inner sheet 11 by means of hot melt adhesive 16 and the free edges 40b are substantially integrated with the lower elastic members 15b by the intermediary of the inner sheet 11. The front member 6 and the rear member 7 are provided with the upper elastic members 15a under tension.

While the side flap 24 comprises the inner cover sheet 31 and the outer cover sheet 32 in the illustrated embodiment, the present invention is not limited to such embodiment and, for example, it is possible to replace the illustrated side flap 24 by the side flap formed by the outer cover sheet 32 alone or the side flap formed by the sheet differing from both the inner cover sheet 31 and the outer cover sheet 32.

The invention claimed is:

1. A disposable pants-type body fluid absorbent wearing article having a longitudinal direction, a transverse direction and a vertical direction being orthogonal one to another, the wearing article comprising:
   front and rear waist regions and a crotch region combined to define a waist-opening and a pair of leg-openings,
   a body fluid absorbent panel extending in said longitudinal direction, wherein the body fluid absorbent panel is affixed to sheet members defining respective inner surfaces of said front and rear waist regions, and wherein said front and rear waist regions are elasticized along a peripheral edge of said waist-opening and respective peripheral edges of said leg-openings,
   said body fluid absorbent panel comprises
      a body fluid absorbent core,
      a liquid-pervious sheet and a liquid-impervious sheet, said core being sandwiched between the liquid-pervious sheet and the liquid-impervious sheet,
      a body fluid absorbent pad extending in said longitudinal direction and bonded to respective said inner surfaces of said front and rear waist regions, and
      flaps formed by the liquid-pervious sheet and the liquid-impervious sheet along side edges of said body fluid absorbent pad and opposed in said transverse direction, said flaps respectively comprising
         proximal edges being contiguous to said side edges of said body fluid absorbent pad and extending in said longitudinal direction and
         free edges, each at a distance from said body fluid absorbent pad in said transverse direction, extending in parallel to said proximal edges, wherein said free edges are provided with first elastic members attached under tension thereto,
   said front and rear waist regions comprise second elastic members extending in the transverse direction, said second elastic members being provided along said peripheral edges of said leg-openings and attached under tension thereto so as to intersect said side edges of said body fluid absorbent pad,
   regions of said flaps in which said free edges of said flaps developed outward in said transverse direction overlap said second elastic members are affixed to said inner surfaces of said front and rear waist regions, and
   an inner surface, facing toward the body fluid absorbent core, of the liquid-pervious sheet and an inner surface of the liquid-impervious sheet are directly bonded together.

2. The body fluid absorbent wearing article as recited by claim 1, wherein said front and rear waist regions as well as said body fluid absorbent panel are shaped in rectangles.

3. The body fluid absorbent wearing article as recited by claim 1, wherein a dimension between said proximal edge and said free edge of each said flap as measured in said transverse direction is in a range of 15 to 50 mm.

4. The body fluid absorbent wearing article as recited by claim 1, wherein the liquid-pervious sheet and the liquid-impervious sheet between the proximal edges and the free edges are directly bonded all the way in the transverse direction to define the flaps.

5. The body fluid absorbent wearing article as recited by claim 1, wherein the first elastic members are sandwiched between the liquid-pervious sheet and the liquid-impervious sheet.

6. The body fluid absorbent wearing article as recited by claim 1, wherein said second elastic members extend in the transverse direction from side edges of said front and rear waist regions to side edges of said core without crossing an entirety of said body fluid absorbent panel.

7. The body fluid absorbent wearing article as recited by claim 1, wherein the body fluid absorbent panel is directly attached to the inner surface of the front and rear waist regions which are arranged on a skin-contacting side of the wearing article.

8. The body fluid absorbent wearing article as recited by claim 1, wherein the first elastic members intersect with the second elastic members at the front and rear waist regions.

9. The body fluid absorbent wearing article as recited by claim 8, the first elastic members are perpendicular to the second elastic members.

10. A disposable pants-type body fluid absorbent wearing article having a longitudinal direction, a transverse direction and a vertical direction being orthogonal one to another, the wearing article comprising:
- front and rear waist regions and a crotch region combined to define a waist-opening and a pair of leg-openings,
- a body fluid absorbent panel extending in said longitudinal direction, wherein the body fluid absorbent panel is affixed to respective inner surfaces of said front and rear waist regions, and wherein said front and rear waist regions are elasticized along a peripheral edge of said waist-opening and respective peripheral edges of said leg-openings, said body fluid absorbent panel comprises
- a body fluid absorbent core,
- a liquid-pervious sheet and a liquid-impervious sheet, said core being sandwiched between the liquid-pervious sheet and the liquid-impervious sheet,
- a body fluid absorbent pad extending in said longitudinal direction and bonded to respective said inner surfaces of said front and rear waist regions and
- flaps formed by the liquid-pervious sheet and the liquid-impervious sheet along side edges of said body fluid absorbent pad and opposed in said transverse direction, said flaps respectively comprising
  - proximal edges being contiguous to said side edges of said body fluid absorbent pad and extending in said longitudinal direction and
  - free edges, each at a distance from said body fluid absorbent pad in said transverse direction, extending in parallel to said proximal edges, wherein said free edges are provided with first elastic members attached under tension thereto, said front and rear waist regions comprise second elastic members provided along said peripheral edges of said leg-openings and attached under tension thereto so as to intersect said side edges of said body fluid absorbent pad, regions of said flaps in which said free edges of said flaps developed outward in said transverse direction overlap said second elastic members are affixed to said inner surfaces of said front and rear waist regions, and an inner surface, facing toward the body fluid absorbent core, of the liquid-pervious sheet and an inner surface of the liquid-impervious sheet are directly bonded together.

* * * * *